United States Patent
Köhler et al.

(10) Patent No.: US 6,497,252 B1
(45) Date of Patent: Dec. 24, 2002

(54) MINIATURIZED FLUID FLOW SWITCH

(75) Inventors: Johann Michael Köhler, Golmsdorf (DE); Torsten Schulz, Jena (DE)

(73) Assignee: Clondiag Chip Technologies GmbH, Jena (DE)

(*) Notice: Subject to any disclaimer, the term of this patent is extended or adjusted under 35 U.S.C. 154(b) by 0 days.

(21) Appl. No.: 09/786,224

(22) PCT Filed: Aug. 26, 1999

(86) PCT No.: PCT/EP99/06380

§ 371 (c)(1),
(2), (4) Date: Mar. 1, 2001

(87) PCT Pub. No.: WO00/12903

PCT Pub. Date: Mar. 9, 2000

(30) Foreign Application Priority Data

Sep. 1, 1998 (DE) ......................................... 198 39 745

(51) Int. Cl.[7] ............................................... F15C 1/04
(52) U.S. Cl. .................. 137/828; 137/833; 137/838; 204/601
(58) Field of Search ................. 137/828, 833, 137/834, 838, 825; 204/601

(56) References Cited

U.S. PATENT DOCUMENTS

| | | | |
|---|---|---|---|
| 3,001,539 A | 9/1961 | Hurvitz | |
| 3,357,441 A | 12/1967 | Adams | |
| 3,361,149 A | * 1/1968 | Meyer | 137/828 |
| 3,452,767 A | * 7/1969 | Posingies | 137/828 |
| 3,494,369 A | * 2/1970 | Inoue | 137/13 |
| 3,552,415 A | 1/1971 | Small | |
| 3,721,255 A | * 3/1973 | Suzuki et al. | 137/807 |
| 3,760,848 A | * 9/1973 | Rehsteiner | 137/828 |

FOREIGN PATENT DOCUMENTS

| | | |
|---|---|---|
| EP | 0745682 | 12/1996 |
| GB | 1241867 | 8/1971 |
| WO | WO 97/47013 | 12/1997 |
| WO | WO 9810267 | 3/1998 |

OTHER PUBLICATIONS

"Electrohydrodynamic Pumping and Flow Measurement" by A. Richter et al., p. 271–276. 1991 IEEE.
Sensors and Actuators, A21–A23, (1990), "Microfabricated Electrohydrodynamic Pumps" by Stephen F. Bart et al., p. 193–197.
"Chemical Analysis and Electrophoresis Systems Integrated on Glass and Silicon Chips" by D. Jed Harrison et al., p. 110–113, 1992 IEEE.
Blankenstein, Scampavia, Branebjerg, Larsen & Ruzicka: "Flow switch for analyte injection and cell/particle sorting" Analytical Methods Instrumentation, Special Issue TAS'96, 1996, pp. 82–84, XP000865501.
Shoji S. et al.: "Microflow devices and systems" Journal of Micromechanics and Microengineering, Dec. 1994, UK. vol. 4, No. 4, pp. 157–171, XP000863761 ISSN: 0960–1317.

* cited by examiner

*Primary Examiner*—A. Michael Chambers
(74) *Attorney, Agent, or Firm*—Jordan and Hamburg LLP

(57) ABSTRACT

The invention relates to a miniaturized fluid flow switch which enables a directed deflection or deviation of a fluidic test current injected into a fluidic carrier current. The aim of the invention it to provide a fluid flow switch which does not require any moveable parts and with which no restricting preconditions exist with regard to the fluid media to be used. To this end, the inventive switch is comprised of at least two carrier current channels (11, 12) and of a test current channel (2) which, together, open into a distribution chamber (3) to which at least two discharge channels (41, 42) connect. The carrier current channels (11, 12) are connected to a common inlet (10), and at least the carrier current channels (11, 12) are respectively placed, in particle sections, in close thermal contact with controllable heating devices (5). Said heating devices are attached such that they are thermally insulated from the remaining components, and in the area of the heating devices (5), the carrier current channels (11, 12) comprise a channel cross section (111, 121) which is narrower than the other carrier current channel cross section.

19 Claims, 2 Drawing Sheets

MINIATURIZED FLUID FLOW SWITCH

BACKGROUND OF THE INVENTION

Figure 1:
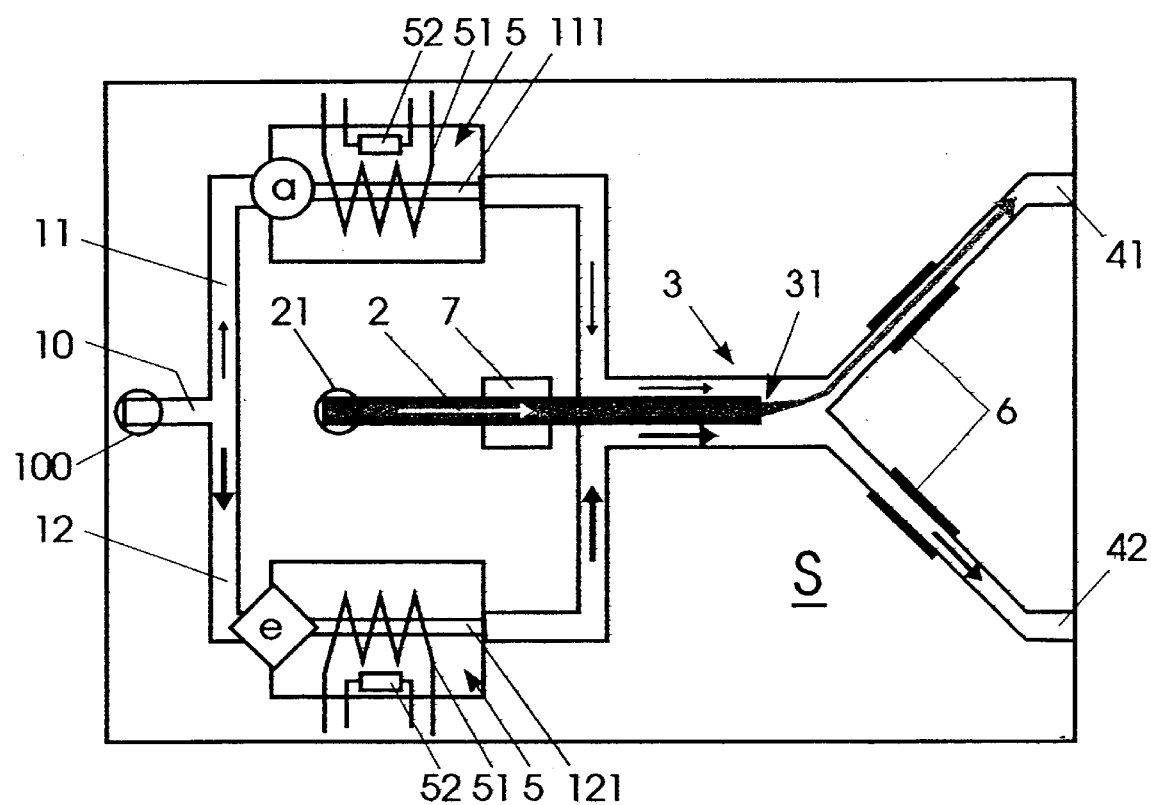

The invention relates to a miniaturized fluid flow switch that enables a directed deflection and discharge of a fluid sample flow that is injected into a fluid carrier flow. The inventional fluid flow switch permits to switch sample flows, and to sort particles, molecules or other substances suspended and dissolved, respectively, in a sample flow according to predetermined criteria.

In G. Blankenstein; L. Scampavia; J. Branebjerg; U. D. Larsen; J. Ruzicka: "Flow Switch for Analyte Injection and Cell/Particle Sorting" in Analytical Methods Instrumentation, Special Issue TAS '96, (1996), pages 82–84, a microsystem technical device is described which comprises two separate carrier flow inputs, one sample flow input, a common flow section which receives all streams, and two outlets. In this approach, the sample flow is directed into several outlet channels via the velocity of flow relation of the two carrier flows. Therein, the velocities of the passage flow in the two carrier flows can be controlled by macroscopic jet pumps. There are, however, no means specified as to sensitively controlling the two carrier flow velocities relative to each other.

A review of the current prior art methods for producing valves, controllable throttles and pumps for the microsystem technique is given in S. Shoji; M. Esashi: "Microflow devices and systems" in J. Micromech. Microeng; 4 (1994), pages 157–171". Nearly all known devices have in common that they require moving parts such as membranes or lips to affect the fluid flow. In the case of electromagnetic or pneumatic procedures the integration of a transducer proves as additionally problematic. Moving parts have the principle disadvantage of a faster aging and a higher susceptibility to trouble. Furthermore, a few methods and devices are known, which do not need any moving parts and which can be used for setting-up pumps in Microsystems. Among these are the electrohydro-dynamic principle [A. Richter, H. Sandmaier: "Electrohydrodynamic pumping and flow measurement", in Proc. IEEE-MEMS Workshop, (1991) pages 99–104], [S. F. Bart, L. S. Tavrow, M. Mehrgany, J. H. Lang: "Microfabricated Electrohydrodynamic pumps", in Sensors Actuators (1990) A21–A23, 193–197], and the electro-osmosis [D. J. Harrison, K. Seiler, A. Manz, Z. Fan: Chemical analysis and electrophoresis systems integrated on glass and silicon chips; Digest of IEEE Solid State Sensor and Actuator Workshop; (1992), 11–113]. These approaches can, however, only very limitedly be used for setting-up a controllable throttle or a valve. Furthermore, the fluids to be pumped or regulated have to satisfy very special conditions when these methods are to be used. The most important conditions are, for example, an extremely low intrinsic conductance (in the case of the electrohydrodynamic), or an extremely high intrinsic conductance and ionic strength, respectively, (in the case of the electro-osmosis). With respect to devices operating on the principle of electro-osmosis there is the additional limitation that the functionality of the device is only ensured when capillaries of a diameter of smaller than 50 $\mu$m are used.

SUMMARY OF THE INVENTION

It is an object of the present invention to provide a miniaturized fluid flow switch, which does not require any moving parts and in which there are no limiting conditions as is the case with the prior art for the fluid media used.

The object is realized by the features of the first claim. Advantageous embodiments are covered by the dependent claims.

The present invention distinguishes itself by the following technical advantages: It is predestined for the integration in microsystems; it can be controlled and operated by electrical signals; and it has no moving, and hence, parts being susceptible to interferences.

The principle of the proposed fluid flow switch resides on the variation of viscosity of a liquid in dependence on the variation of its temperature. When the fluid is heated in predetermined sections of a duct by way of an electric resistance heating, then its hydrodynamic resistance changes in response. In the case of the electro-caloric fluid control, electro-caloric throttles are used for control of a carrier fluid which is used to distribute a sample liquid to different channels. In the simplest case, the carrier flow is pumped into a channel which symmetrically branches into two channels. One section of each of these two carrier flow channels is of a reduced channel cross-section related to the remaining channel cross-section of the carrier flow, whereby the reduced channel cross-section is provided with a controllable heating device. Furthermore, the carrier flow channel sections are thermally insulated relative to the other components of the fluid flow switch. The carrier flow channels funnel into the head of a distributor chamber together with the sample channel.

The distributor chamber is designed in minor-symmetry to the sample channel. At least two outlet channels are provided at the end of the distributor chamber. The sample fluid is injected right into one of the provided outlet channels by actuating the heating device provided. The relation of the velocity of flow in the two carrier flows decides at the inlet of the distributor chamber, into which of the provided outlet channels the sample fluid is pressed.

DETAILED DESCRIPTION OF THE INVENTION

Figure 2:
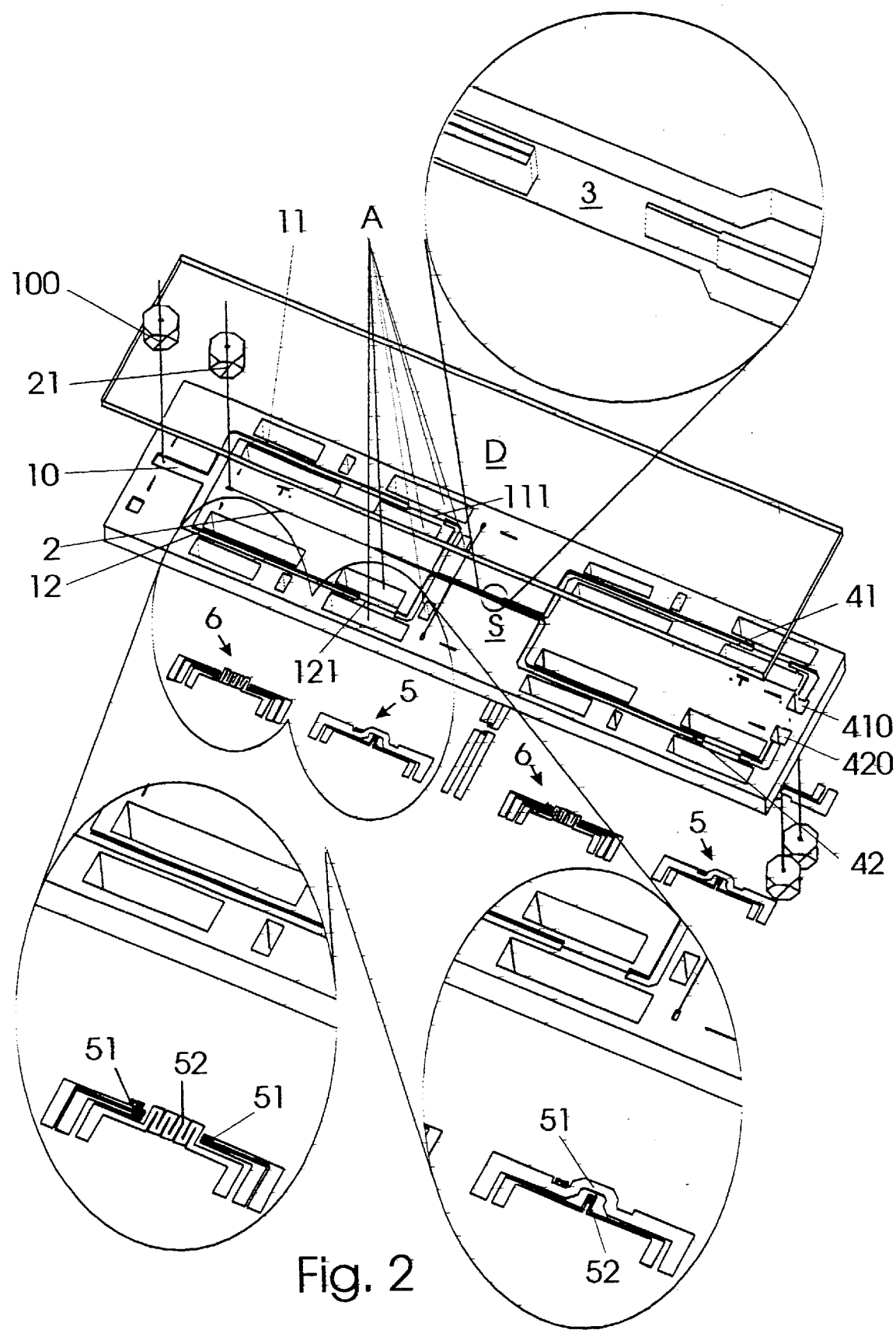

The invention will be explained in more detail by virtue of schematical embodiments. There is shown in:

FIG. 1 a plan view of a principle embodiment of a miniaturized fluid flow switch including the substantial operational components;

FIG. 2 an explosive view of a more detailed embodiment with further operational components.

FIG. 1 in a plan view shows a substrate S into which a carrier flow channel 10 is inserted which is symmetrical split into two carrier flow channels 11, 12 that are given a width of 0.5 mm and a depth of 50 $\mu$m. In preselected zones, the carrier flow channels 11, 12 are provided with carrier flow channels 11 1, 121 of reduced cross-section compared to the remaining carrier flow channel cross-section. In the example, these reduced cross-sections have a width of 10 $\mu$m and a depth of 5 $\mu$m. Furthermore, these partial carrier flow sections are in a narrow thermal contact with controllable heating devices 5, which preferably are formed by a thin layer resistance heater 51 and a thermo-sensor 52. The mentioned carrier flow sections are thermally insulated from the other components of the fluid flow switch by means which are not shown in detail in FIG. 1. The outlets of the mentioned partial carrier flow sections again run along sections for the carrier flow of non-reduced cross-section and commonly funnel into a distributor chamber 3, whereby they symmetrically include a sample fluid channel 2 that also flows into the distributor chamber 3. In the example, the sample fluid channel is given thereby a width of 100 $\mu$m and a depth of 50 $\mu$m which matches the depth of the carrier flow channels, and the sample fluid channel is embedded into the substrate S just as the carrier flow channels. In the head 31 of the distributor chamber, there is a section provided in which the two carrier flows that enclose the sample fluid flow in common. At and to the end of the distributor chamber 3, at least two outlet channels 41, 42 are connected that, in the example according to FIG. 1, are provided with flowmeters 6, the output signals of which are adapted to be also fed into a common control and regulation of the heating devices 5. When one of the heating devices 5 are switched ON and thus the thin layer heater 51 is set into operation, as is schematically indicated in FIG. 1 by an "e" enclosed by a square upright standing on a corner, then the hydrodynamic resistance is reduced in the respective carrier flow channel 12. The portion of carrier flow liquid which now flows through this channel section will increase compared to the portion which can flow through the carrier flow channel 11, which is not heated in the example (refer to FIG. 1, to the encircles "a"). The result is that the sample injected into the distributor chamber 3 is pressed into the outlet channel 41. When, vice versa, the heating device 5 in the carrier flow channel 11 is switched ON, the sample flows into the outlet channel 42.

It lies within the scope of the invention, to split up the carrier flow channel 10 into more than two channels which can also be provided with different channel cross-sections. Thereby, however, at least two respective partial channels, symmetrically associated to each other, are given identical cross-sections. The resulting partial channels can all be provided with one of the mentioned controllable heating devices 5 so that there is in the distributor chamber 3 the possibility given to very precisely direct the sample flow. Thereby, it also lies within the scope of the invention to provide more than only two outlet channels at the end of the distributor chamber 3. Furthermore, the outlet channels can be provided with channel sections of reduced cross-section (in analogy to sections 111 and 121) and heating devices 5 (not shown in FIG. 1) associated to the channel sections of reduced cross-section. In this manner the deflecting/ directing effect in the distributor chamber 3 can be further increased and adjusted more finely. When in the example according to FIG. 1, the heating device in the carrier flow channel 12 and, in the outlet channel 41, an analogous heating device at a channel section, similarly designed as the channel section 121, would be switched ON, then the sample fluid could be pressed into the outlet 41 in a still more defined manner.

The miniaturized fluid flow switch can also be used for sorting particles, molecules, or other substances suspended, respectively dissolved in the sample flow. To this end a detector 7 is integrated or preceding in series in the sample channel 2. When there is a desired particle under test detected, then the particle is pressed into the desired outlet by actuating the respectively provided heating device. Thereby it does not matter according to which characteristic, for example, size, color, fluorescent spectrum, dielectric, conductance, radioactivity, chemical reactivity etc. shall be sorted; there has to be installed only a detector 7 that detects the values mentioned. Generally, the miniaturized fluid flow switch can be used for all tasks in which sample flows are to be distributed to carrier flows (fluid multiplexing). When within the scope of the invention there is spoken of fluid media, then thereunder are also, expressis verbis, gases to be understood that form the carrier flow and the sample fluid. The thermal insulation, not shown in more detail in FIG. 1, of the heating device from its ambience, whereby the heating device is provided in the channel section of reduced cross-section, and the use of materials with a good thermal conductivity for thermally coupling to the reduced channel cross-section are employed to increase the operation speed.

In FIG. 2 a microsystem technical embodiment of a miniaturized fluid flow switch will be elucidated by way of an explosive view in more detail. In this example, the miniaturized fluid flow switch comprises a silicon chip S of a size of 15 mm·60 mm, into which channels 10, 11, 12, 111, 121, 2, 41, 42, the distributor chamber 3, and thermal insulation zones, here in the form of passing-through recesses A, which have been inserted by anisotropic wet-chemical two-stage deep etching. In this example the channels 11, 12, 2, 41, and 42 have the dimensions as mentioned in connection with FIG. 1 and are not given to scale in FIG. 2, either. The units mentioned in the present example are covered by a Pyrex glass wafer D of 0.2 mm thickness, whereby these are preferably sealed to the substrate S by anodic bonding. The channels are opened to the outside by deep etching or ultrasonic boring, or the like, through the substrate S and the covering waver D, respectively, in order to establish connections 100, 21, 410, 420 for the respective channels to the outside. Aluminium connection fittings are adhered onto the formed openings which are adapted for external connectors, not shown in more detail, to the channels.

Platinum coats and aluminium coats are deposited on the bottom-side of the silicon chip S. In these platinum and aluminium coats the structures for formation of the thin layer resistance heating 51 and of the thin layer thermo-sensors 52 are produced by means of usual microlithographic procedures.

The thin layer heating resistors 51, having a resistance of about 10Ω and being operated with maximally 36 W, are associated to the channel sections 111, 121 of reduced cross-section which are located in the range of the heating devices 5. The thin layer thermo-sensors 52 that are adapted for temperature control, have a resistance of about 2.2 kΩ and a TK of 0.00198 K$^{-1}$. Recesses A are provided in the silicon substrate S on at least both sides of the channels 111, 121 of reduced cross-section in order to thermally insulate the range of the heating device from the remaining units.

In the example according to FIG. 2, the carrier flow channel 10 again is split up into two channels 111, 121. In a further design related to FIG. 1, a flowmeter 6 is provided in each of said channels, whereby this flowmeter is preceding the reduced cross-section channels described. Preferably, the flowmeter is produced in thin layer technique in one operation, just as the structurizing of the thin layer resistance heaters 51 and the thin layer thermo-sensors 52. The principle of the flowmeter is based on the measurement of the distortion of the temperature profile of a heater, which two temperature feelers are symmetrically associated to, whereby this distortion is caused by the heat transport effect of the fluid flowing in the channel.

To contribute to the above mentioned further increase of sensitivity of the directing/deflecting of the sample flow in the head 31 of the distributor chamber 3, one flowmeter 6 each as well as one reduced cross-section channel with associated heating device are coordinated to the two outlet channels 41, 42 in this example. The formation of these flowmeters is carried out in analogy to those described above.

A miniaturized fluid flow switch according to the embodiments described permits the realization of a switching speed of 5 Hz, without any problems.

In the present invention all required components can be very easily placed on one chip, in particular on a silicon chip. Hence, the miniaturized fluid flow switch is a proper and complete microsystem. Moreover, the fluid flow switch according to the invention does without any moving parts and, thus, is extremely non-susceptible to interferences.

All features disclosed in the specification, in the subsequent claims, and in the drawing can be substantial for the invention both, individually and in any combination with one another.

LIST OF REFERENCE NUMERALS

10—carrier flow channel (common inlet)
100—carrier flow input
111, 121—carrier flow channels
111, 121—reduced channel cross-sections
2—sample fluid channel
21—channel connection to outside (sample fluid input)
3—distributor chamber
31—head of distributor chamber
41, 42—outlet channels
410, 420—connections
5—heating device
51—thin layer heating resistor/resistance heater
52—thermo-sensor
6—flowmeter
7—detector
A—recesses
D—covering wafer
S—substrate/silicon wafer
a, e—switching position

What is claimed is:

1. A fluid flow switch for directed deflection of a sample fluid using a carrier fluid, comprising:
   at least two carrier flow channels having a common carrier fluid input for receiving said carrier fluid;
   a sample fluid channel having a sample fluid input, independent of said common carrier fluid input, for receiving said sample fluid;
   a distributor chamber having said sample fluid channel communicated therewith for receiving a flow of said sample fluid, said distributor chamber also having said at least two carrier flow channels communicated therewith for steering said flow of said sample fluid by flows of said carrier fluid;
   at least two outlet channels communicating with said distributor chamber and disposed to selectively receive said flow of said sample fluid in dependence on said steering by flows of said carrier fluid; and
   controllable heating devices provided in close thermal contact with respective ones of said carrier flow channels for selectively heating said flows of said carrier fluid in said carrier flow channel to control viscosity of said flows of said carrier fluid to effect said steering.

2. The fluid flow switch as claimed in claim 1, wherein the carrier flow channels symmetrically enclose the sample fluid channel by extending along opposing walls of said sample fluid channel at least in the distributor chamber.

3. The fluid flow switch as claimed in claim 1, wherein the sample fluid and carrier flow channels and the distributor chamber are formed in a common substrate and are closed by a closing wafer.

4. The fluid flow switch as claimed in claim 3, further comprising recesses in said substrate disposed adjacent said controllable heating devices to effect thermal insulation thereof.

5. The fluid flow switch as claimed in claim 1, wherein the outlet channels are provided with controllable heating devices in close thermal contact therewith.

6. The fluid flow switch as claimed in claim 1, wherein at least one of the carrier flow channels and the outlet channels are provided with flowmeters.

7. The fluid flow switch as claimed in claim 6, wherein the flowmeters include an electrically heatable thin layer heater and two temperature sensors for measuring thermal distribution in said thin layer heater.

8. The fluid flow switch as claimed in claim 1, further comprising at least one detector is associated with the sample fluid channel for detecting single particles in the fluid sample flow and providing output signals to effect control of said heating devices.

9. A miniaturized fluid flow switch for directed deflection of a sample fluid using a carrier fluid, comprising:
   at least two carrier flow channels having a common carrier fluid input for receiving said carrier fluid;
   a sample fluid channel having a sample fluid input, independent of said common carrier fluid input, for receiving said sample fluid;
   a distributor chamber having said sample fluid channel communicated therewith for receiving a flow of said sample fluid, said distributor chamber also having said at least two carrier flow channels communicated therewith for steering said flow of said sample fluid by flows of said carrier fluid;
   at least two outlet channels communicating with said distributor chamber and disposed to selectively receive said flow of said sample fluid in dependence on said steering by flows of said carrier fluid;
   said carrier flow channels each having a reduced cross section portion, having a cross section smaller than other portions of said carrier flow channels; and
   controllable heating devices provided in close thermal contact with respective ones of said reduce cross section portions of said carrier flow channels and thermally insulated relative to remaining portions of said fluid flow switch.

10. Miniaturized fluid flow switch as claimed in claim 9, wherein the carrier flow channels symmetrically enclose the sample fluid channel by extending along opposing walls of said sample fluid channel at least in the distributor chamber.

11. Miniaturized fluid flow switch as claimed in claim 9, wherein the carrier flow channels are given in identical flow cross-section.

12. Miniaturized fluid flow switch as claimed in claim 9, wherein the sample fluid and carrier flow channels and the distributor chamber are formed in a common substrate and are closed by a closing wafer.

13. Miniaturized fluid flow switch as claimed in claim 12, wherein the thermal insulation of the controllable heating devices from the remaining components comprises recesses formed in the substrate on sides of said reduce cross section portions.

14. Miniaturized fluid flow switch as claimed in claim 9, wherein the outlet channels are provided with controllable heating devices in close thermal contact therewith.

15. Miniaturized fluid flow switch as claimed in claim 9 or 14, wherein the controllable heating devices are formed by a thin layer heating resistor and a thin layer thermo-sensor.

16. Miniaturized fluid flow switch as claimed in claim 15, wherein said thin layer heating resistor and thin layer thermo-sensor are manufactured by use of a same coating technology and a common microstructurizing process.

17. Miniaturized fluid flow switch as claimed in claim 9, wherein at least one of the carrier flow channels and the outlet channels are provided with flowmeters.

18. Miniaturized fluid flow switch as claimed in claim 17, wherein the flowmeters include an electrically heatable thin layer heater to which two temperature sensors are symmetrically associated in channel flow direction.

19. Miniaturized fluid flow switch as claimed in claim 9, wherein at least one detector is associated with the sample fluid channel for detecting single particles in the sample flow and the output signals of said detector are adapted to control said heating devices via control and regulating devices.

* * * * *